United States Patent [19]

Lengyel et al.

[11] Patent Number: 4,671,266

[45] Date of Patent: Jun. 9, 1987

[54] BLISTER BANDAGE

[75] Inventors: Stephen P. Lengyel, Medfield; John M. Greenway, Westwood, both of Mass.

[73] Assignee: The Kendall Company, Boston, Mass.

[21] Appl. No.: 826,443

[22] Filed: Feb. 5, 1986

[51] Int. Cl.⁴ ............................................ A61L 15/00
[52] U.S. Cl. .................................................... 128/156
[58] Field of Search .......................................... 128/156

[56] References Cited

U.S. PATENT DOCUMENTS

| | | | |
|---|---|---|---|
| 2,140,026 | 12/1938 | Murphy et al. | 128/156 UX |
| 2,241,384 | 5/1941 | Bateman et al. | 128/156 |
| 2,592,801 | 4/1952 | Hanington | 128/156 |
| 2,740,402 | 4/1956 | Scholl | 128/156 |
| 4,112,177 | 9/1978 | Salditt | 128/156 |
| 4,133,310 | 1/1979 | Lloyd | 128/156 |
| 4,310,509 | 1/1982 | Berglund | 128/156 |
| 4,349,020 | 9/1982 | Krikorian | 128/156 |
| 4,411,754 | 10/1983 | Kaetsu | 128/156 |
| 4,460,369 | 7/1984 | Seymour | 128/156 |
| 4,460,642 | 7/1984 | Errede | 128/156 |

Primary Examiner—Gregory E. McNeill
Attorney, Agent, or Firm—Francis J. Clark

[57] ABSTRACT

A blister bandage comprising at least one ply of an aerated latex microsized hydroentangled fabric, having an adhesive disposed on at least one surface of said fabric. The present invention has sufficient hydrophobicity in the fabric to be a barrier to liquid borne bacteria while preserving comfort, air permeability, and flexibility therein. In addition to the above properties, the bandage is sterilizable and will keep the skin beneath the bandage dry.

3 Claims, 5 Drawing Figures

4,671,266

BLISTER BANDAGE

BACKGROUND OF THE INVENTION

This invention relates generally to protective coverings for wounds, blisters and the like, or as a preventive covering in areas of the skin where blisters tend to form, to prevent blisters from forming. It relates especially to a blister bandage that has high oxygen permeability, but is a liquid barrier, is flexible, strong, and a bacteria barrier. Today, bandages and wound dressings consist of many different forms. One bandage such as that made by Johnson & Johnson under the Tradename "Bandaid", has an outer layer or backing of a porous plastic film having an adhesive and a nonwoven pad attached to the films inner surface. When the bandage is applied to a patient the nonwoven pad is placed over a blister and comes into contact with the skin. The porous plastic film backing in the prior art is supposedly used to let moisture, that is trapped under the bandage, evaporate out through the pores in it. This is usually not the case, because although there are pores in the bandage, moisture trapped under the bandage against the skin does not evaporate out through them. This is quite evident in a visual observation of the skin after the bandage has been removed, because the skin is moist and wrinkled. This condition is mainly due to the fact that the pores in the plastic film only allow air to circulate in areas where the pores are. When moisture is trapped close to the skin it causes the skin to remain moist, thereby wrinkling the skin. If the skin remains moist, a blister or wound may be subjected to bacteria and a long healing time. In addition, this type of prior art bandage, if used as a protective covering to protect against blisters forming, will trap moisture, such as perspiration against the skin. This will keep the skin moist and make the skin subject to blisters. This is a condition that would not be tolerated by the wearer of this type bandage.

Another prior art bandage, is that such as described in U.S Pat. No. 3,247,845, wherein a bandage fabric, made from silk or cotton, is impregnated with a flexible collodion solution, which is then dried. When applying this bandage, the collodion solution must be redissolved in situ over the wound with an appropriate solvent. This type of bandage has many disadvantages. One such disadvantage is that it is only effective when used to cover a blister that has already formed. Another disadvantage is that a solvent must be used to activate the solution within the bandage, before the bandage becomes effective. Still another disadvantage is that this type of bandage requires a person to carry both a bandage and a solvent in their possession to properly use it.

In U.S. Pat. No. 4,296,499, there is described a foot covering article that is worn over the bare foot, underneath a sock, to prevent the formation of blisters. This prior art device is comprised of a single, porous, nonwoven sheet which is formed into a foot enveloping shape. There is a disadvantage associated with this article because it is obviously expensive to manufacture, and to purchase. It is, in essence, another sock to cover the foot.

The prior art has tried to achieve the aforementioned properties of air permeability, liquid barrier, flexibility, strength and a bacteria barrier in blister bandages, but has been unsuccessful. The present invention has achieved these properties by using a unique fabric structure that is superior to the prior art.

SUMMARY OF THE INVENTION

The present invention relates to a blister bandage, comprising an aerated latex microsized hydroentangled fabric having an adhesive disposed on at least one surface of said fabric. Microsizing is defined herein as the application of a chemical froth to a fabric to create microsize pores therein, which are necessary to establish a bacterial barrier in a fabric while preserving air permeability. The particular properties of this fabric allow the fabric to remain soft, air permeable, flexible and strong. The fabric structure also makes the fabric conducive to providing a bacterial barrier with hydrophobicity, thus lending itself for use as a blister bandage.

An object of this invention is to provide a bandage that can be produced economically.

Another object of this invention is to provide a bandage substantially more conformable and comfortable than prior art bandages.

Still another object of this invention is to provide a bandage that is uniformly breathable, due to the better air permeability of said bandage, while at the same time repelling liquid and bacteria.

An additional object of this invention is to provide a bandage with strength and flexibility.

Still another object of this invention is to provide a bandage that is substantially free of lint.

Another object of this invention is to provide a bandage that is sterilizable.

A further object of this invention is to provide protection without adding bulk or padding to a bandage.

Other objects will be apparent from the remainder of the specifications and claims.

DESCRIPTION OF PREFERRED EMBODIMENT

Figure 1:
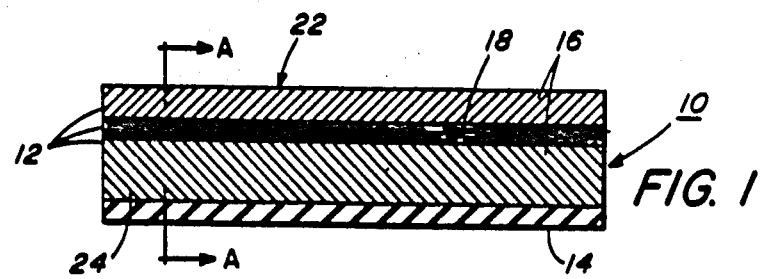
FIG. 1 illustrates a sectional view of a single ply microsized hydroentangled bandage fabric and a pressure sensitive adhesive.
Figure 3:
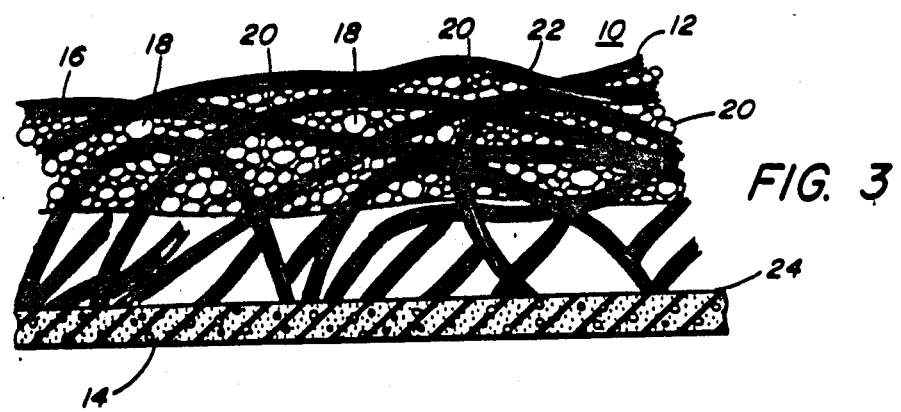
FIG. 3 illustrates the porous structure of the present embodiment, which is a further magnified view of FIG. 1.

FIG. 1 illustrates a blister bandage 10, comprising a microsized fabric 12, as described in U.S. Pat. No. 4,499,139 of common assignee, and herein incorporated by reference, and an adhesive 14 disposed on at least one surface of said fabric. As shown in FIGS. 1 and 3, the microsized fabric 12 consists of hydroentangled textile length fibers 16 having a latex microporous froth sizing 18 within the fiber structure. Hydroentangling of nonwoven material is done by subjecting a fibrous web of textile length fibers to a series of high pressure water jets, to entangle the fibers therein. Froth sizing, as described in U.S. Pat. No. 4,499,139, is a latex mixture that is aerated by an Oakes Foamer. Due to the extremely low cost of the materials used in the present invention, it is more economical to produce than prior art bandages. In addition to hydroentangled fabrics, any woven or nonwoven material may also function as a blister bandage material when made according to U.S. Pat. No. 4,499,139. Although the preferred embodiment is to be used as a blister bandage, it may be used wherever a protective covering is needed.

For purposes of this invention where we speak of bacterial barriers, we mean materials constructed in such a manner so as to prevent bacteria from penetrating through them.

Research has shown that a blister is formed on the skin by a shear force being exerted thereon. The shear force exerted upon the skin causes the epidermis layer of the skin to separate from the dermis layer. When these layers separate, liquid forms between them, to produce a blister. Therefore, if the shear force can be reduced or eliminated, blisters will not form.

Application of the present invention blister bandage to a potential site of a blister will help to prevent a blister forming. The bandage will act as a protective covering, and will also decrease the frictional activity, which create the shear force. This reduction of friction is essentially due to the inner surface of the bandage being soft and pliable, thus allowing it to move with the skin. Additionally, because there is no material attached to the inner surface of the fabric, it will not cause irritation or apply pressure to the skin.

In addition, fibers on the outer layer of the present invention have a low coefficient of friction, thus will slide across other surfaces reducing any shear force caused by movement within footwear or clothes. Furthermore, since the present invention is not as bulky as prior art, there is no additional pressure put on the blister area, or potential blister site.

The present invention bandage made from the referenced microsized fabric has the look and feel of a cloth. Because the referenced microsized fabric has the qualities of a cloth, it is conformable, comfortable, and flexible. To check for softness, conformability, or comfort of a fabric, tests are available which are discussed herein. The test for softness and conformablity is conducted according to the Industrial Nonwoven Disposable Association Standard Test, IST 90.0-75(R77). The test is a Softness Handle-O-Meter test where forces are used to bend the fabric to determine the drape, conformability, hand and softness. In addition, to insure the fabric is comfortable, an internal test is performed, which is called a Cytotoxic Test. The Cytotoxic Test is actually a battery of tests which insures that the fibers and other components used on or within the fabric are non-irrating when placed against human skin. The present invention fabric passed these tests. A flexibility test is performed in accordance with the Industrial Nonwoven Disposable Association Standard Test, IST30.0-70(R77), and the American Society of Testing Materials, ASTM D774-67. The test for flexibility is called the Mullen Burst Test, whereby a circular diaphragm is placed against the fabric to be tested. Pressure is then applied to the diaphragm until the fabric ruptures. The present invention also retains substantial strength due to its hydroentangled construction. The strength tests are conducted in accordance with IST 110.0-70(R77), ASTM D1682.64 and ASTM D2261-71. The strength tests consist of a Tongue Test and a tensile strength test. The Tongue Test, tests the ability of the fabric not to tear. In this test, the fabric is cut into a rectangular piece 3 inches wide by 8 inches long. The rectangular piece of fabric is then slit in the center, half way down the fabric in the 3 inch width direction. The two ends of the slit piece are then attached to an Instron Tester (a tensile strength test machine made by Instron Corporation of Canton, Mass.) and subjected to a tearing force. This force is then recorded. The tensile strength test consists of taking a strip of fabric one inch wide by eight inches long and attaching said strip to an Instron tester. A force is exerted by the tester in the vertical direction to determine what force it takes to break or tear the fabric. When the fabric breaks, the force is then recorded.

Figure 2:
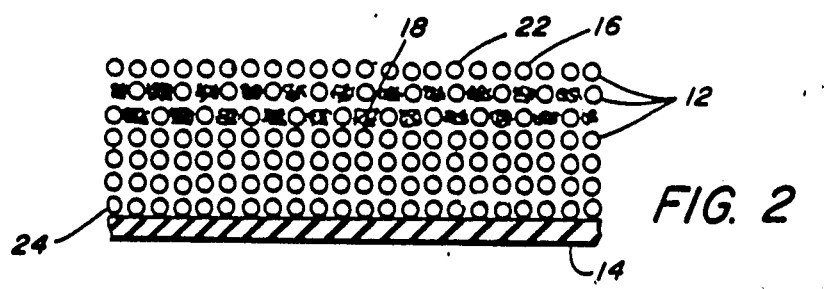
FIG. 2 shows a magnified sectional view of FIG. 1, along line AA.

A unique stratification of the present fabric essentially makes a two-sided fabric, as shown in FIG. 3 wherein, the outer surface fibers 22 of the fabric 12 are subjected to latex froth sizing 18 to give a protective coating, while the inner surface fibers 24 of the fabric remain substantially froth free and thus pliable and soft. The inner surface fibers 24 as shown in FIGS. 1, 2 and 3 are then coated with a porous pressure sensitive adhesive 14 to complete the bandage. The adhesive 14 on the fabric 12, as shown in FIG. 1, can be applied to the inner surface fibers 24 of the fabric 12 by knife application, reverse roll application or other conventional procedures.

The adhesive that is applied to the microsized fabric can be any porous solvent base pressure sensitive adhesive such as a polyacrylate. Such a porous adhesive may have pore sizes that range between 10 microns and 100 microns. However, it is preferred that the pore size in the adhesive be between 25 to 40 microns. Although other types of adhesives may be used, the preferred adhesive is used because it has a structure that lends itself to air permeability. This enhances the air circulation in the bandage produced thereby. Air circulation is an important property of a bandage and will be discussed in detail in subsequent paragraphs. Although the inner surface fibers are coated with an adhesive, they remain relatively soft and pliable. This is due to the porous nature of the adhesive and the fact that the inner surface fibers are not coated with the froth. In addition, because the fabric is hydroentangled and has a froth sizing within it, it is virtually lint free. Furthermore, because it is lint free, there are no air borne or loose fibers that would contaminate an open blister or wound, or that would contribute to the cause of a blister. To determine the amount of lint present in a fabric a test is conducted that consists of rubbing a Number Zero emery cloth against both surfaces of the fabric in a circular motion using at least 15 cycles. The number of cycles it takes to raise fibers is then recorded. No lint was detected in the present invention bandage after the test.

Referring to the drawings, FIG. 3 shows the micropores 20 of the froth sizing 18 situated between and adjacent to the top surface fibers 22 of the fabric. Micropores may be defined as open pores ranging in size from 10 to 100 microns. As described in U.S. Pat. No. 4,499,139, of common assignee, these pores are created by dispersing air, which creates air bubbles, in a latex liquid. The frothed liquid, once deposited on a fabric, is then heated to solidify the latex. The heat in curing the latex bursts the air bubbles thereby creating the micropores. These micropores 20 created from the froth 18 are important for two reasons. The first is that these micropores 20 allow the free movement of air through the fabric. In other words, these micropores 20 give substantial air permeability to the fabric. An air permeability test is conducted according to the Industrial Nonwoven Disposble Association Standard Test IST 70.1-70(R77) and Federal method 5452, referred to as the Frazier Test. The Frazier Test consist of passing a certain volume of air through a certain area of fabric per unit time under a low pressure differential. Thus, the greater the volume of air passed through a fabric, the higher the air permeability.

When moisture is created by a covered wound or blister, it is essential that this moisture be allowed to escape away from the wound or blister out through the covering. This cannot be done unless the bandage material used has substantial air permeability. Thus, air permeability is an important property of a bandage. Air permeability in a bandage material permits moisture that is formed on the wearer's skin under a bandage, to evaporate, and to be carried by the circulation of air, out through the bandage. More important, air permeability in a bandage material substantially eliminates maceration of the skin. Maceration is defined for the purpose of this application as the puckering, wrinkling and whitening of the skin due to the prolonged exposure of moisture to the skin. Confinement of moisture on the skin usually results from covering skin for a prolonged period of time with a bandage material. The present invention bandage does not allow maceration to take place because the total bandage material is quite air permeable, thus allowing substantial evaporation to occur, and causing the skin to remain substantially dry. In addition, the dryness of the skin aids in reducing the cause of blisters. Furthermore, the finished fabric, because of its air permeability, is highly sterilizable.

An air permeability test was performed between the present invention bandage and a prior art bandage made by Johnson and Johnson under the Tradename "Bandaid," which is one of the presently accepted bandages for blisters. It was found that the prior art bandage had a higher air permeability than the present invention, as measured by a Frazier Test. This is indicated in the following test results.

| Sample | Air Permeability FT3/FT2/Min. |
| --- | --- |
| Micro sized blister bandage (with adhesive) | 25 |
| Prior Art Bandage (J&J) | 102 |

Figure 4:
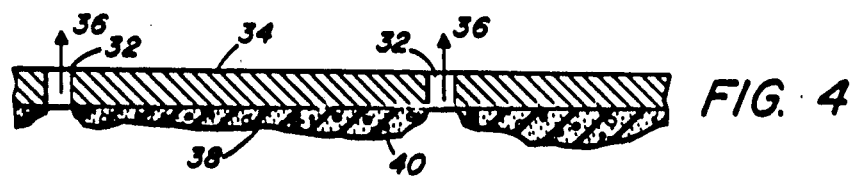
FIG. 4 is a sectional view of a prior art bandage, and further shows the buildups of moisture thereunder.
Figure 5:
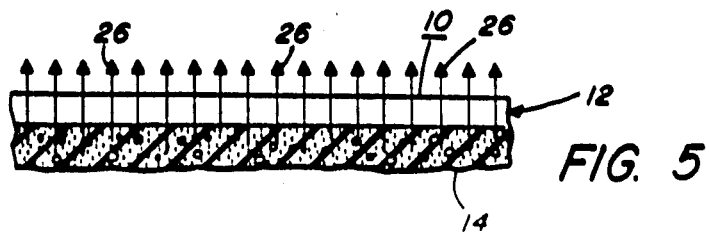
FIG. 5 further illustrates the present invention, and the permeability of the bandage, by showing moisture evaporating out through the pores in the bandage fabric.

Although this may seem to illustrate that the prior art would function better than the present invention, it was observed that the prior art bandage macerated the skin, while the present invention bandage did not. This lack of maceration of the skin by the present invention was an unexpected result. It has been determined that because the prior art pores or perforations 32 are isolated from each other, as illustrated in FIG. 4, moisture 38 remained trapped under the adhesive 40 of the prior art bandage 34, in the areas between the pores 32, when the bandage is applied to the skin. This does not promote good air circulation 36, as illustrated in FIG. 4. Very little, if any evaporation of moisture takes place, thus maceration of the skin is visibly present. On the other hand, as shown in FIG. 5, the present invention bandage 10, because of its microporous structure 12 and the porous adhesive 14, has uniform air permeability 26 throughout the fabric. This overall air permeability contributes to substantial evaporation of any moisture against the skin thus eliminating maceration of the skin. Thus, the present invention is superior over prior art, notwithstanding the fact that the prior art bandage material apparently was more "air permeable" than the bandage material of this invention.

In addition to providing excellent air permeability, micropores, such as described herein, are important because they provide a barrier on the outside surface of the fabric against liquid borne bacteria. It is believed that this is done by stopping the flow of liquid, which may have bacteria in it, through the fabric, by a capillary action force on the micropores which counteracts the driving force caused by a head of liquid. By preventing liquid from penetrating a bandage, a blister or wound will remain isolated from any bacteria or liquid present. Thus, this is another advantage the present invention has over the prior art. FIG. 4 illustrates the large size openings 32 that are evident in visual inspection of the prior art. These large openings 32 allow liquid to freely enter into the bandage. FIGS. 3 and 5 show the present invention, and illustrate that the pores within the present invention are of micro proportion which are not evident by a visual inspection. As explained in the following tests, the micropores of the present invention repell liquid but do not allow it to enter through the bandage itself.

To determine whether a fabric can hold back liquid, it is subjected to two tests—the Mason Jar Test and the Hydrostatic Head Test. The Mason Jar test is conducted according to the Industrial Nonwoven Disposable Association Standard Test, IST 80.7-70(R77), and the Hydrostatic Head Test is conducted according to the American Association of Textile Chemists and Colorists, AATCC-127-1974 and IST 80.0-70(R77). The Mason Jar Test determines the time it takes liquid to through penetrate the fabric when said fabric is under a head of water of 4.5 inches, and the Hydrostatic Head Test determines the amount of water pressure the fabric can withstand before water passes through said fabric.

It should be noted that the microsized fabric of the present invention bandage satisfactorily passed all the aforementioned tests, as is evident in Table 1.

The following is an example of the present embodiment, and is not intended to limit the present invention, except as to the claims.

EXAMPLE 1

A 40.8 (gsy) grams per square yard 100% polyester hydroentangled fabric, such as sold by DuPont Inc., located in Delaware, and identified as P004 was microsized in a continuous process by applying, via a knife-over-roll applicator, an ethyl-butyl acrylate-clay froth of the composition as described in the aforementioned U.S. Pat. No. 4,499,139.

The froth applied in this Example was first aerated by an Oakes Foamer, Model No. 4MT2A to a density of approximately 160 grams per liter by rotating the mixing head at 1125 revolutions per minute and pumping at a setting of 180 (approximately 200 grams per minute). The back pressure at the foamer was 55 pounds per square inch of gage. The froth was fed batch-wise in 5-10 minute intervals to the knife-over-roll applicator. The gap between the knife and roll was set at 11 mils. The fabric weighed 40.8 gsy (grams per square yard) before microsizing and 53.5 gsy thereafter.

The process line speed was 10 feet per minute. After applying the froth, the microsized web was dried in an air circulating oven with three zones set at 210° F., 225° F., and 250° F., respectively. The sizing penetrating into the fabric, was 60-80 microns of the total 300 micron fabric thickness. The outer surface fibers 22 as shown in FIGS. 1, 2 and 3 were substantially left uncoated. The average pore size was between 20 and 40 microns, with a few pores at 80 microns.

The fabric was then passed thru a knife-over-roll applicator, whereby a porous solvent base synthetic polyacrylate pressure sensitive adhesive was applied to the inner surface fibers 24 of the fabric as shown in FIG. 1, 2 and 3. The adhesive was then cured by passing the composite fabric through an oven. After curing, the fabric was slit into specific bandage widths and wound into rolls.

TABLE 1
PROPERTIES OF MICROSIZED FABRIC

| PROPERTY | HOSPITAL ACCEPTABLE VALUES | EXAMPLE 1 |
|---|---|---|
| Weight per area, gsy | 50-60 | 53.5 |
| Tensile strength, lb | | |
| MD (Machine Direction) | 15* | 40.4 |
| CD (Cross Direction) | 12* | 13.4 |
| Elongation at break, % | | |
| MD | — | 25.6 |
| CD | — | 183.3 |
| Mullen Burst, psi | 30* | 57.8 |
| Tongue Tear, lbs | | |
| MD peak | — | 2.0 |
| Average | 1.5* | 1.5 |
| CD | 1.5* | no tear |
| Energy to tear, inch-lb | — | 8.9 |

TABLE 1-continued
PROPERTIES OF MICROSIZED FABRIC

| PROPERTY | HOSPITAL ACCEPTABLE VALUES | EXAMPLE 1 |
|---|---|---|
| Handle-o-meter, gm force | | |
| MD | — | 85.7 |
| CD | — | 8.1 |
| Overall | 50** | 47 |
| Air Permeability, (Without Adhesive) | | |
| Frazier | | |
| cuft/sqft/min | 50* | 103.5 |
| Hydrostatic Head, inches of water | 9* | 9.5 |
| Mason Jar Test, min. (5 samples required) | 60* 120+ | 60+ |
| Abrasion, cycles to 1st pill | | |
| Outer Face | 15* | 22 |
| Inner Face | 15* | 26.2 |
| Cytotoxic Test (Living tissue test) | Passed | Passed |

*minimum value
**maximum value

What is claimed is:

1. A blister bandage comprising at least one ply of an aerated latex microsized porous entangled nonwoven bacterial barrier fabric, having an adhesive disposed on at least one surface of said fabric.

2. The blister bandage of claim 1 wherein said adhesive is a porous pressure sensitive adhesive.

3. The blister bandage of claim 2 wherein said adhesive is a porous polyacrylate.

* * * * *